United States Patent [19]

O'Brien

[11] 4,062,829

[45] Dec. 13, 1977

[54] POLYESTER COMPOSITIONS AND METHODS OF STABILIZING SAME

[75] Inventor: William L. O'Brien, Cincinnati, Ohio

[73] Assignee: Emery Industries, Inc., Cincinnati, Ohio

[21] Appl. No.: 739,500

[22] Filed: Nov. 8, 1976

[51] Int. Cl.² .............................................. C08K 5/53
[52] U.S. Cl. .......................... 260/45.85 T; 260/75 P; 260/941
[58] Field of Search ................ 260/45.85 T, 941, 75 P

[56] References Cited

U.S. PATENT DOCUMENTS

| | | | |
|---|---|---|---|
| 2,988,558 | 6/1961 | Swern et al. | 260/941 |
| 3,196,190 | 7/1965 | Nischk et al. | 260/941 |
| 3,639,538 | 2/1972 | Kleiner | 260/941 |
| 3,776,884 | 12/1973 | Spivack | 260/45.85 |

*Primary Examiner*—V.P. Hoke
*Attorney, Agent, or Firm*—Wood, Herron & Evans

[57] ABSTRACT

Polyester compositions containing organophosphorus derivatives as stabilizers are disclosed. Methods of stabilizing polyesters are also provided by incorporating the organophosphorus derivatives during processing to prevent thermal and catalytic decomposition, and with improvements in resin color, molecular weight retention and mechanical properties. This invention also affords an efficient method of inhibiting the decomposition activity of the first stage catalyst in the production of high polymeric condensation polyester resins.

9 Claims, No Drawings

POLYESTER COMPOSITIONS AND METHODS OF STABILIZING SAME

BACKGROUND OF THE INVENTION

Polyester resins are derived from glycols and dicarboxylic acids by condensation reactions. In processing the reactants through polymerization, there are principally two stages involved, i.e., a first stage of transesterification and a second stage of polycondensation in which the reactants are converted to high polymeric condensation polyester resins. Under the thermal and catalytic conditions of the polymerization, there is a tendency for the polymer that is being formed to undergo decomposition. Polymer decomposition is evidenced by loss in molecular weight, liberation of carboxyl end groups giving rise to an increase in acid value, coloration of the polymer melt and deterioration of mechanical properties.

The effects of interesterification catalysts upon the instability of polyester resins have been reported upon, for example, in H. Zimmerman, Faserforschung u. textiltechnik, 13, 481 (1962). Catalysts not only promote transesterification and polycondensation but also induce various modes of thermal decomposition of the polyester resin. More specifically, in the conversion of dimethyl terephthalate to bis 2-hydroxyethyl terephthalate, the reaction is promoted through the equilibrating action of catalysts such as zinc acetate dihydrate, calcium acetate hydrate, manganese acetate tetrahydrate, and others. Conversion to maximum viscosity polyester is efficiently accomplished by catalysts such as lead (II) acetate and oxide, titanates and, in particular, antimony compounds such as antimony (III) oxide and acetate. A combination of catalysts is usually indispensible to commercially accetable polymerization conditions. However, with such catalytic combinations, polymer decomposition results as evidenced by viscosity drop, coloration, etc., as mentioned above.

Thus, it has been proposed to incorporate additives both during and after polymerization to improve the stability of polyester resins. For example, U.S. Pat. No. 3,676,393 is directed to stabilizer additives of simple organic phosphonates, phosphonites and phosphinites in polyester compositions. Other additives such as organic phosphates and ammonium phosphates have been employed. Generally, there are a number of difficulties associated with employment of the known additives. For example, in the addition of rather simple phosphonates or phosphonites, there is a tendency for such derivatives to distill out under polymerization conditions essential to high polymeric resin formation. In addition, some of the known derivatives tend to be extremely susceptible to unsatisfactory rearrangement reactions, and interfere with polymerization, or undergo thermal elimination reactions. With respect to known arylphosphonites or phosphonates, while they possess a certain amount of volatility, the aryl groups tend to be cleaved by acids and are detrimental to polymer color. Furthermore, when the molecular weight of known simple phosphorus derivatives is increased to reduce volatility, the phosphorus content of the derivatives is reduced thereby reducing their effectiveness. Suffice it to say that the prior art approaches to reduce the instability of polyester resins have not been completely satisfactory.

SUMMARY OF THE INVENTION

This invention is directed to polyester resin compositions having enhanced stability by the incorporation therein of an effective amount of an organophosphorus compound selected from the group consisting of compounds having the following formula and polycondensates thereof,

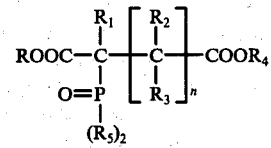

in which R and $R_4$ are selected from the group consisting of alkyl, aralkyl, cycloalkyl, alkcycloalkyl, hydroxyalkyl, hydroxyaralkyl, hydroxyalkylether and hydroxyaralkylether, where R or $R_4$ is at least one of said hydroxyl terminated groups; where $R_1$, $R_2$ and $R_3$ are selected from the group of hydrogen and alkyl; where $R_5$ is selected from the group of an alkyl, aryl, alkaryl, cycloalkyl, alkcycloalkyl, alkoxy, aralkyl and aralkoxy; and $n$ is 1 or greater.

It has been found that organophosphorus compounds of the above class offer advantages heretofore unobtainable by stabilizers of the prior art in preventing decomposition of high polymeric polyester resins. The stabilizers of the present invention are not fugitive under polyester processing conditions, and therefore are very advantageously employed during the first stage transesterification and polycondensation essential to the conversion of the monomers and ligamers to high polymers. Stabilizers of this invention are polymerizable to polyester processing temperatures of higher molecular weight phosphorus-containing condensates which are nonvolatile. It has also been discovered in this connection that certain of the stabilizers can be incorporated during processing and as much as 75%–100% of phosphorus which is introduced via the stabilizer composition is retained in the finished polyester resin. Higher phosphorus retention is generally an indicia of better stability. In contrast to stabilizers of the prior art, these organophosphorus compounds offer a higher phosphorus content with increasing molecular weight, among other advantages. Thus, stabilized polyester resin compositions according to this invention are very useful in polyester fiber formation where destabilization of the resin is especially a problem.

In another of its aspects, this invention is directed to a method of polymer stabilization during formation of high molecular weight polyester condensation resins. As developed above, during the formation of high polymeric resins, the reactants undergo high temperature and low pressure conditions in the presence of various catalysts which are effectively employed respectively in the first stage of transesterification or second stage of polycondensation. It has been found that the organophosphorus stabilizers of this invention are very effectively employed at the end of the transesterification step to inhibit the depolymerization effects of the first stage catalyst during polycondensation. Furthermore, even though the organophosphorus derivatives of this invention are very effective inhibitors of the first stage catalyst, the second or polycondensation stage of the reaction may be conducted with another very efficient catalyst to achieve high molecular weight polymer. Accordingly, this invention offers a unique method of stabilizing polyester resins during their formation.

The organophosphorus stabilizers employed in accordance with the present invention are prepared by the straight forward reaction of an unsaturated dicarboxylic acid and a polyhydric alcohol to produce a semi-ester. Thereafter, the semi-ester is reacted with a trialkyl, aryl or mixed alkyl/aryl phosphite, for example, to produce hydroxy termination phosphorus-containing esters. A number of suitable polycarboxylic acids may be employed in their preparation, however, it is preferred to use an alpha, beta-unsaturated dicarboxylic acid. Suitable polycarboxylic acids are, for example, maleic acid, methylene-succinc acid, fumaric acid, glutaconic acid, α-hydromuconic acid, β-hydromuconic acid, methylene malonic acid and the like. A number of suitable polyhydric alcohols may be employed such as, for example, ethylene glycol, 1,3-propylene glycol, 1,4-butylene glycol, 1,6-hexane diol, 1,5-pentane diol, neopentyl glycol, dimethylol cyclohexane, cyclohexane diol, diethylene glycol, triethylene glycol, mixtures of said glycols, xylene diol, and the like. Therefore, the acids and the glycols may be varied in the preparation of the stabilizers. Presently, for example, both di- and triethylene glycols have been found to provide excellent phosphorus retention in the finished polyester resin of at least about 80% or better. Ethylene glycol provides phosphorus retention values of about 60%. Therefore, based upon present results, for greater phosphorus retention, it is preferred to use the di- or triethylene glycol and, of these two, the diethylene glycol for the best compromise from the standpoint of phosphorus retention and color.

The phosphorus compounds which are reacted with the semi-esters to produce the organophosphorus compounds of this invention include the trifunctional phosphites, phosphonites or phosphinites. In general, such derivatives have the formulas $P(OR)_3$; $(RO)_2P R$ or $(RO)PR_2$ wherein R is alkyl, aryl, aralkyl, alkaryl and mixed groups thereof. For example, where phosphites are employed in the reaction with the semi-esters, at least one R radical is alkyl such that the transesterification involving alkylation and rearrangement with the compounds containing active unsaturation may take place. A number of these phosphites can be used and examples falling within the above formula are butyl phenyl phosphite, diheptyl phenyl phosphite, butyl diphenyl phosphite, isobutyl diphenyl phosphite, hexyl diphenyl phosphite, amyl ditolyl phosphite, octyl diphenyl phosphite, trixylyl phosphite, dibenzyl phenyl phosphite, dodecyl diphenyl phosphite, nonyl diphenyl phosphite, and so forth. The organic phosphorus reactants are well known to the art. They can readily be derived from mixtures of alcohols and/or phenols, substituted phenols and so forth by reaction with phosphorus trichloride and separating the resulting organic chloride from the organic phosphite.

Whereas the organophosphorus stabilizers of this invention may be made by other techniques, the above reaction is preferred because it is straightforward. For example, the organophosphorus containing compounds are produced by reacting a polyhydric alcohol with an alpha, beta-unsaturated dicarboxylic acid in a first stage to form the corresponding unsaturated semi-ester. The molar ratio of the carboxylic acid to polyhydric alcohol is controlled so that the hydroxy terminated semi-ester is formed. Thereafter, the reaction mixture is cooled and a corresponding quantity of trialkyl phosphite is incrementally added for conversion to the organophosphorus derivative until the acidity approaches 0, whereupon alcohol may be stripped from the reaction mixture. The stripped alcohol corresponds to the alkyl radical of the phosphite which was split off by transesterification.

The polyester resins stabilized according to the principles of this invention are derived from a glycol and a dicarboxylic acid or ester thereof. These polyesters are high polymeric condensation resins. Representative examples of polyesters include polyethylene terephthalate, polytetramethylene terephthalate, polycyclohexane dimethanol terephthalate, polyethylene dibenzoate, copolyesters of terephthalic acid, an aliphatic dicarboxylic acid and a glycol, etc. Dicarboxylic acids from which the resins can be derived are dicarboxylic acids such as oxalic acid, malonic acid, succinic acid, glutaric acid, adipic acid, pimelic acid, suberic acid, azelaic acid, sebacic acid, brassylic acid, thapsic acid, diethylsuccinic acid, isophthalic acid, terephthalic acid, hemimellitic acid. The resins can be made from various glycols, including ethylene glycol, propylene glycol, butylene glycol, pentamethylene glycol, hexamethylene glycol, decamethylene glycol, diethylene glycol, 1,4-cyclohexane dimethanol, etc. Such condensation polyesters, particularly those based upon terephthalic acid and ethylene glycol are very well known. The latter is preferred because of its low cost and ready availability, but the effectiveness of this invention is not limited to these examples.

The polyester resins are prepared in accordance with known techniques by reacting the bis esters of the acids with the glycols under ester interchange conditions to form glycol esters or low polymers thereof. These products are then polymerized under condensation polymerizartion conditions to form high molecular weight polymer. If desired, the glycol esters can be prepared by some other suitable method and then polymerized to form high molecular weight polymer. The reactions are preferably carried out in an atmosphere of inert gas such as nitrogen and to facilitate preparation of high molecular weight colorless products. The condensation reaction is usually carried out under reduced pressure, generally below about 10 mm of mercury pressure, and usually at a temperature in the range of from about 260° to 290° C. The reactants are condensed to polyesters having an intrinsic viscosity of on the order of at least about 0.3 to about 0.6. In the preparation of the polyester resin as developed above various catalysts can be used. Catalysts which are suitable for use in the ester interchange reaction include zinc acetate, calcium acetate, manganese acetate, and other catalytic salts of zinc, manganese, magnesium, calcium, sodium and potassium. Of those catalysts which can be used for conversion of the polyester to maximum viscosity are lead acetate and oxide, organo-titanates, antimony oxide, antimony acetate, and other metal salts of lead, antimony, and the like referred to in the above identified publications.

The polyester resins are stabilized by the addition of the organophosphorus compounds of this invention in concentrations ranging from a minimum effective amount of about 0.01 to about 1% by weight based upon the weight of the resin. Above 1%, the economics tend to govern the amounts of added stabilizer and, possibly with such increased amounts of the organophosphorus, disadvantageous side effects on other additives including dyes and other components come into consideration. In view of the high phosphorus content of the organophosphorus derivatives, the organophosphorus stabilizer can be used in the low range of about 0.01 to about 1% and increased stability is achieved as manifested by the retention of light color, molecular weight and tensile properties. As developed above, the stabilizer is usually introduced during formation of the resin from low molecular weight components. The organophosphorus additive inhibits the activity of the first stage catalyst. Therefore, it is preferably added at the end of the first stage. However, it has also been found that the stabilizer can be added after the polyethylene terephthalate resin is formed in the second stage of polycondensation and thermal stabilization effects can be obtained. A typical example of the preparation of polyethylene terephthalate by the DMT process (dimethyl terephthalate) involves the following technique. In the first stage, the monomer, bis 2-hydroxyethyl terephthalate is prepared for example by reacting 10.3 mols of dimethyl terephthalate with 22.6 mols of ethylene glycol employing 0.3 or .009% by weight of zinc acetate catalyst. The dimethyl terephthalate is reacted with the ethylene glycol and catalyst with agitation for about 5 hours to a maximum temperature of about 210° C. During this time the theoretical amount of methanol distills over. At this point, the stabilizer of this invention is added to deactivate the first stage catalyst. During the second stage the polyethylene terephthalate is prepared by reacting the bis 2-hydroxyethyl terephthalate in a polymerization or polycondensation reaction in the presence of a second stage catalyst such as the antimony oxide in an amount of about 0.25% by weight. The materials are reacted with agitation in a stainless steel reactor at about 280° C and 0.5mm vacuum until the desired viscosity is obtained.

The invention will be further understood with reference to the following Examples. Examples 1–7 illustrate the preparation of the organophosphorus stabilizers of this invention.

EXAMPLE 1

Ethyl 2-hydroxyethyl alpha-diethylphosphonosuccinate

Fumaric acid (1740 grams, 15.0 mols) and ethylene glycol (930 grams, 15.0 mols) were placed in a 12 liter flask equipped with a glass/teflon stirrer, a simple glass Vigreux column and still head, a thermometer-thermostat, and a pressure equalizing dropping funnel. Hypophosphorous acid was added in an amount of about 0.1%. The resulting charge was heated at about 145°–150° C for about 1.5 hours, during which approximately 220 mls. of distillate were collected at 98°–102° C; at that point, the acid value of the mixture was 346 mg KOH/gram. The esterification product thus obtained was cooled to 55° C and triethylphosphite (2490 grams, 15.0 mols) was added through the dropping funnel at a rate such that the temperature did not exceed about 60° C. The addition required 12 hours and the acid value at completion of phosphite introduction was 55–75 mg KOH/gram. The product was finished by heating at 75°–95° C until an acid value of 2.0 was obtained. Introduction of additional phosphite to assist the process was optional. Volatile matter was removed by applying evacuation to ca 5mm mercury and heating the reaction vessel to about 100°–150° C. Typical ranges of analytical values for the stabilizer products produced according to reaction were: acid value 0.7–2; hydroxyl 35–60%; triethylphosphite, less than about 0.5%; phosphorus, about 9–11.

EXAMPLE 2

Ethyl 2-hydroxyethoxyethyl alpha-diethylphosphonosuccinate

The procedure according to Example 1 was repeated using similar apparatus and under essentially similar conditions allowing for the differences in quantities of materials employed. In this example, the following materials were substituted for those of the previous example: 4.0 mols of fumaric acid, 4.0 mols of diethyleneglycol, 4.0 mols of triethylphosphite and 0.05% of hypophosphorous acid. The product of the reaction had an acid value of about 0.6, hydroxyl value of 34, less than about 0.1% triethylphosphite and a phosphorus content of about 9.2%.

EXAMPLE 3

Ethyl 2-hydroxyhexyl alpha-diethylphosphonosuccinate

The procedures according to Example 1 were repeated using similar apparatus and under essentially similar conditions allowing for the differences in quantities of materials employed. In this example, for the materials of Example 1, 1 mol fumaric acid, 1 mol of 1,6-hexane diol, 0.1% of hypophosphorous acid and 1 mol of triethylphosphite were employed. The product of the reaction had analytical values for acid value, hydroxyl, free triethylphosphite and phosphorus content comparable to those reported in Example 1.

EXAMPLE 4

Ethyl 2-(hydroxyethyl-hydroxyethoxyethyl) alpha-diethylphosphonosuccinate

The procedure according to Example 1 was repeated using similar apparatus and under essentially similar conditions allowing for the differences in quantities of materials employed. In this example, for the materials of the previous Example 1, 6.0 mols fumaric acid, 3.0 mols of ethylene glycol and 3.0 mols of diethylene glycol, 0.1% of hypophosphorous acid and 3.0 mols of triethylphosphite were employed. The product of the reaction had analytical values comparable to those reported for Example 1.

EXAMPLE 5

Ethyl 2-(2-hydroxyethoxy) oxydiethylene alpha-diethylphosphonosuccinate

The procedure according to Example 1 was repeated using similar apparatus and under essentially similar conditions allowing for the differences in quantities of materials employed. In this example, for the materials of the previous Example 1, 4.0 mols of fumaric acid, 4.0 mols of triethyleneglycol, 4.0 mols of triethylphosphite and 0.5% of hypophosphorous acid were employed. The product of the reaction had an acid value of about 5, a hydroxyl value of about 34, triethylphosphite less than 0.1% and a phosphorus content of about 7.3%.

EXAMPLE 6

Ethyl 3-hydroxyneopentyl alpha-diethylphosphonosuccinate

The procedure according to Example 1 was repeated using similar apparatus and under essentially similar conditions allowing for the differences in quantities of materials employed. In this example, for the materials of the previous Example 1, 2.0 mols of fumaric acid, 2.2 mols neopentylglycol, 2.0 mols triethylphosphite and 0.5% of hypophosphorous acid were employed. The product of the reaction had analytical values comparable to those reported in Example 1.

EXAMPLE 7

Ethyl 2-hydroxypropyl alpha-diethylphosphonosuccinate

The procedure according to Example 1 was repeated using similar apparatus and under essentially similar conditions allowing for the differences in quantities of materials employed. In this example, for the materials of Example 1, 1 mol fumaric acid, 1 mol of propylene glycol, 0.1% of hypophosphorous acid and 1 mol of triethylphosphite were employed. The product of the reaction had analytical values of acid value, hydroxyl, free triethylphosphite and phosphorus content comparable to those reported in Example 1.

The following examples illustrate the improvements of color and thermal stabilities in polyethylene terephthalate made with the inclusion of organophosphorus stabilizer in accordance with the principles of this invention.

EXAMPLE 8

Bis 2-hydroxyethyl terephthalate monomer was prepared according to the technique described above from dimethyl terephthalate employing manganous acetate (0.035% by weight based upon dimethyl terephthalate). Thereafter, 2500 grams of bis 2-hydroxyethyl terephthalate monomer containing 2.3 grams of ethyl 2-hydroxyethoxyethyl alpha-diethylphosphonosuccinate (containing 8.7% phosphorus) was charged along with 0.03% by weight of antimony (III) oxide into a 1 gallon reactor. The reaction mixture was polymerized for approximately 5 hours at 230°–280° C and with a vacuum of less than about 1 mm Hg. A polymer sample initially discharged under nitrogen pressure at this point in reaction showed good color and the polymer sample had an inherent viscosity of 0.57 d/g measured at 30° C in a mixed solvent of 60/40 phenol-tetrachloroethylene by volume. The remaining polymer was then stirred at 280° C for an additional 45 minutes under nitrogen but without vacuum. The good color of the polymer after this period of time was maintained and the product showed no apparent viscosity drop. Accordingly, by employing the organophosphorus stabilizer of this invention at the end of the first stage transesterification, good color was obtained in the finished polymer and, as evidenced by the retention of molecular weight, the depolymerizing activity of the first stage catalyst was inhibited.

A control reaction was performed for comparison with the above reaction. In this case, the controlled reaction was identical in all respects except that there was no organophosphorus stabilizer incorporated at the end of the first stage processing. Therefore, under identical conditions after the first 5 hours of polymerization, the inherent viscosity of the control was about 0.46 d/g and was light yellow in color. Therefore, in comparison to the stabilized processing conditions of this invention, the viscosity of the controlled polymer was less, i.e., about 0.11 d/g than the stabilized resin after five hours. This indicated that the depolymerization or decomposition activity of the first stage catalyst was taking place, as further evidenced by the melt yellow color. After 45 minutes at about 280° C under nitrogen without vacuum, the controlled reaction mixture exhibited a viscosity drop from 0.46 to 0.42 d/g indicating that further depolymerization by the uninhibited catalyst occurred; and the color of the finished product was yellow. These results indicate that without the stabilizer of this invention, upon further heating, simulating remelt of the finished polymer of the reaction, decomposition of the finished polymer takes place. Whereas, in contrast, with the stabilizer of this invention, stability is achieved.

Further illustrating the principles of this invention, other stabilizer compositions were employed in polyester synthesis and the effects on the course of such synthesis were observed. A series of experiments were carried out in glass tubes according to the method of Whinfield et al., British Pat. No. 578,079 (1946). Using such procedures, polyethylene terephthalate was synthesized in a manner quite similar to the above described technique and employing different stabilizer compositions of this invention. A standard polymerization time of about three hours was employed with a final vapor bath temperature of about 290°–294° C. The catalysts employed were manganous acetate and antimony (III) oxide as the ester interchange and polymerization catalysts, respectively. The organophosphorus stabilizer component was added at the end of the first stage reaction in an amount such that 100 ppm phosphorus was contained based upon the dimethyl terephthalate. In the following table, the stabilizer compositions employed, the phosphorus retention in polyethylene terephthalate, the inherent viscosity in the finished polymer and the melt colors are provided.

TABLE I

| Stabilizer Composition of Example No. | Phosphorus Retention (ppm) ± 10% | Inherent Viscosity (dl/g) | melt Color |
|---|---|---|---|
| 1 | 54 | 0.60 | Good |
| 2 | 100 | 0.53 | Good |
| 6 | 25 | 0.59 | Light Yellow |
| 7 | 105 | 0.54 | Good |

Thus, in employing various organophosphorus stabilizers of the above examples, in all cases the inherent viscosity near about 0.6 was obtained. The phosphorus retention values of a significant order of magnitude were achieved and the melt color was good in all cases except for the neopentyl derivative which was light yellow. These results demonstrate that the fumarate half-ester may be varied and the objectives of this invention can still be achieved.

The above Example 8 illustrates the preferred approach for improving color and thermal stability of polyethylene terephthalate, i.e., by incorporating the stabilizer at the end of ester interchange reaction of dimethyl terephthalate and ethylene glycol. The stabilizer of the present invention can also be added after the polyethylene terephthalate resin has been formed. The following table indicates the addition point of the stabilizer of Example 8 and the results obtained from thermal stability tests on samples of the polymer. The thermal stability tests were carried out at 282° C under nitrogen atmosphere for 2 hours. The inherent viscosities of both initial and degraded polymer samples were determined. The percent of broken linkages as a measure of thermal stability were then calculated for each sample of resin according to the following formula as described in U.S. Pat. No. 3,676,393. Sample 1 was a polymer sample without stabilizer. In samples 2 and 3, the stabilizer was added at the end of the ester interchange and after the polymer had been formed, respectively.

$$\text{Percent of broken linkages} = \frac{N_{in} - N \text{ degraded}}{N_{in} \times N \text{ degraded}} \times C \times 100$$

In which $N_{in}$ = inherent viscosity of the polymer before thermal degradation, $N$ degraded = inherent viscosity after thermal treatment, $C$ = a factor which depends on the viscosity range of the sample. The following average values of $C$ were used in these calculations:

| N Range | Correction Factor, C |
|---|---|
| 0.30 – .50 | 0.435 |
| 0.55 – 0.65 | 0.409 |

TABLE II

| Sample | Stabilizer Added (PPM Phosphorus) | Point of Addition | Inherent Viscosity Initial | Inherent Viscosity After Thermal Treatment | % Broken Linkages |
|---|---|---|---|---|---|
| 1 | — | — | 0.39 | 0.33 | 20.2 |
| 2 | 100 | End of ester interchange | 0.63 | 0.58 | 5.6 |
| 3 | 100 | After polymer had been formed | 0.46 | 0.41 | 11.5 |

The above results demonstrated that the thermal stability was best improved upon the addition of stabilizer at the end of the ester interchange, i.e., by comparison of 20.2% broken linkages with only 5.6% broken linkages upon such stabilization. It was also demonstrated that the thermal stability could still be improved upon the addition of the stabilizer after the polymer was formed, though to a lesser extent.

The above examples are illustrative of the principles of this invention and are not to be considered limitations on this invention.

What is claimed is:

1. A polyester resin composition comprising
a high polymeric condensation thermoplastic polyester resin of a dicarboxylic acid and a glycol and,
as a stabilizer thereof in an effective amount an organophosphorus compound selected from the group consisting of compounds having the following formula and polycondensates thereof

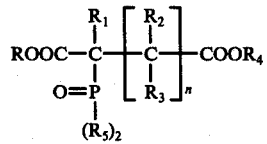

wherein R and $R_4$ are selected from the group consisting of alkyl, aralkyl, cycloalkyl, alkcycloalkyl, hydroxyalkyl, hydroxyaralkyl, hydroxyalkylether and hydroxyaralkylether, where R or $R_4$ is at least one of said hydroxyl terminated groups; where $R_1$, $R_2$ and $R_3$ are selected from the group of hydrogen and alkyl; where $R_5$ is selected from the group of alkyl, aryl, alkaryl, cycloalkyl, alkcycloalkyl, alkoxy, aralkyl and aralkoxy; and $n$ is 1 or greater.

2. The composition of claim 1 wherein said effective amount is on the order of about 0.1 to about 1% by weight based upon said resin.

3. The composition of claim 1 wherein said stabilizer is selected from the group consisting of ethyl 2-hydroxyethyl alpha-diethylphosphonosuccinate, ethyl 2-hydroxyethoxyethyl alpha-diethylphosphonosuccinate, ethyl 2-hydroxyhexyl alpha-diethylphosphonosuccinate, ethyl 2-(hydroxyethyl-hydroxyethoxyethyl) alpha-diethylphosphonosuccinate, ethyl 2-(triethyleneglycol) alpha-diethylphosphonosuccinate, ethyl 2-hydroxyneopentyl alpha-diethylphosphonosuccinate and ethyl 2-hydroxypropyl alpha-diethylphosphonosuccinate, and mixtures thereof.

4. The composition of claim 1 wherein said acid comprises terephthalic acid and said glycol comprises ethylene glycol.

5. The composition of claim 1 wherein said polyester resin is selected from the group consisting of polyesters and copolyesters of terephthalic acid.

6. A method for the preparation of high polymeric condensation thermoplastic polyester resins comprising
transesterifying in a first stage a dicarboxylic acid ester with a glycol in the presence of a catalyst,
adding to the product of said transesterification an effective amount of an organophosphorus compound selected from the group consisting of compounds having the following formula and polycondensates thereof

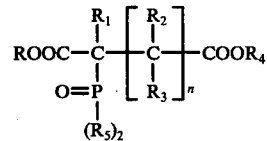

wherein R and $R_4$ are selected from the group consisting of alkyl, aralkyl, cycloalkyl, alkcycloalkyl, hydroxyalkyl, hydroxyaralkyl, hydroxyalkylether and hydroxyaralkylether, where R or $R_4$ is at least one of said hydroxyl terminated groups; where $R_1$, $R_2$ and $R_3$ are selected from the group of hydrogen and alkyl; where $R_5$ is selected from the group of alkyl, aryl, alkaryl, cycloalkyl, alkcycloalkyl, alkoxy, aralkyl and aralkoxy; and $n$ is 1 or greater
and polycondensating the reaction product of said transesterification to produce the high polymeric polyester resin.

7. The method of claim 6 wherein the dicarboxylic acid ester is derived from terephthalic acid.

8. The method of claim 6 wherein said effective amount is on the order of about 0.1 to about 1% by weight based upon said acid ester.

9. The method of claim 6 wherein said stabilizer is selected from the group consisting of ethyl 2-hydroxyethyl alpha-diethylphosphonosuccinate, ethyl 2-hydroxyethoxyethyl alpha-diethylphosphonosuccinate, ethyl 2-hydroxyhexyl alpha-diethylphosphonosuccinate, ethyl 2-(hydroxyethyl-hydroxyethoxyethyl) alpha-diethylphosphonosuccinate, ethyl 2-(triethyleneglycol) alpha-diethylphosphonosuccinate, ethyl 2-hydroxyneopentyl alpha-diethylphosphonosuccinate and ethyl 2-hydroxypropyl alpha-diethylphosphonosuccinate, and mixtures thereof.

* * * * *

UNITED STATES PATENT AND TRADEMARK OFFICE
CERTIFICATE OF CORRECTION

PATENT NO. : 4,062,829

DATED : December 13, 1977

INVENTOR(S) : William L. O'Brien

It is certified that error appears in the above-identified patent and that said Letters Patent are hereby corrected as shown below:

Col. 1, line 37 "accetable" should be --acceptable--

Col. 2, line 35 "to" should be --at--

Col. 2, line 36 "of" should be --to--

Col. 5, line 65 "ca" should be --<u>ca</u>--

Col. 7, line 18 "of" should be --for--

Col. 7, line 42 "d/g" should be --dl/g--

Col. 7, line 61 "d/g" should be --dl/g--

Col. 7, line 65 "d/g" should be --dl/g--

Col. 8, line 3 "d/g" should be --dl/g--

UNITED STATES PATENT AND TRADEMARK OFFICE
CERTIFICATE OF CORRECTION

Page 2 of 2

PATENT NO. : 4,062,829
DATED : December 13, 1977
INVENTOR(S) : William L. O'Brien It is certified that error appears in the above-identified patent and that said Letters Patent are hereby corrected as shown below:

Col. 8, line 37 "melt" should be --Melt--

Col. 9, line 42 "thereof" should be --therefor--

Signed and Sealed this

Ninth Day of May 1978

[SEAL]

Attest:

RUTH C. MASON
Attesting Officer

LUTRELLE F. PARKER
Acting Commissioner of Patents and Trademarks